United States Patent [19]

Lashier

[11] Patent Number: 5,859,303

[45] Date of Patent: Jan. 12, 1999

[54] OLEFIN PRODUCTION

[75] Inventor: Mark E. Lashier, Lake Jackson, Tex.

[73] Assignee: Phillips Petroleum Company, Bartlesville, Okla.

[21] Appl. No.: 574,031

[22] Filed: Dec. 18, 1995

[51] Int. Cl.$^6$ .................................... C07C 2/30
[52] U.S. Cl. .............. 585/513; 585/510; 585/511; 585/512; 585/516; 585/520; 585/521; 585/522; 585/523; 585/525; 585/530; 585/531; 585/532
[58] Field of Search .................. 585/510, 511, 585/512, 516, 520, 521, 522, 523, 525, 530, 531, 532

[56] References Cited

U.S. PATENT DOCUMENTS

| | | | |
|---|---|---|---|
| 4,668,838 | 5/1987 | Briggs | 585/513 |
| 4,716,206 | 12/1987 | Fujita et al. | 526/139 |
| 4,777,315 | 10/1988 | Levine et al. | 585/512 |
| 4,853,356 | 8/1989 | Briggs | 502/117 |
| 5,198,563 | 3/1993 | Reagen et al. | 556/57 |
| 5,288,823 | 2/1994 | Reagen et al. | 526/124 |
| 5,331,104 | 7/1994 | Reagen et al. | 585/512 |
| 5,376,612 | 12/1994 | Reagen et al. | 502/104 |
| 5,382,738 | 1/1995 | Reagen et al. | 585/512 |
| 5,438,027 | 8/1995 | Reagen et al. | 502/117 |
| 5,470,926 | 11/1995 | Reagen et al. | 526/120 |
| 5,491,272 | 2/1996 | Tanaka et al. | 585/520 |
| 5,523,507 | 6/1996 | Reagen et al. | 585/513 |

FOREIGN PATENT DOCUMENTS

| | | |
|---|---|---|
| 0 668 105 | 8/1995 | European Pat. Off. . |
| 0 699 648 | 3/1996 | European Pat. Off. . |
| 2 271 116 | 4/1994 | United Kingdom . |

OTHER PUBLICATIONS

Briggs, John R.; *J. Chem. Soc., Chem. Couumn.*, "The Selective Trimerization of Ethylene to Hex–1–ene" (1989) pp. 674–675.

*Primary Examiner*—Elizabeth D Wood
*Attorney, Agent, or Firm*—Lynda S. Jolly

[57] ABSTRACT

A process is provided to trimerize or oligomerize olefins in the presence of an olefin oligomerization catalyst and a solvent which is a product of the olefin oligomerization process.

16 Claims, No Drawings

OLEFIN PRODUCTION

BACKGROUND OF THE INVENTION

This invention relates to olefin production.

Olefins, primarily alpha-olefins, have many uses. For example, alpha-olefins, such as 1-hexene, can be used in hydroformulation (OXO processes). In addition to uses as specific chemicals, alpha-olefins can be used in polymerization processes as either a monomer or comonomer to prepare polyolefins, or polymers. Often the production of olefins is carried out in the presence of a solvent, or a diluent. Unfortunately the presence of such a solvent or diluent complicates an olefin production process by requiring the presence of an additional chemical, i.e., the solvent, which therefore necessitates piping and control systems for the solvent. Additional processing step(s) in order to separate the desired olefin product from the solvent, as well as solvent recovery and/or disposal, also can be necessary.

SUMMARY OF THE INVENTION

Accordingly, it is an object of this invention to provide an improved olefin production processes.

It is a further object of this invention to provide an improved olefin trimerization process.

It is yet another object of this invention to provide an improved olefin oligomerization process.

It is still a further object of this invention to provide a process to trimerize olefins in a minimal amount, or absence, of a solvent.

It is another object of this invention to provide a process to oligomerize olefins in a minimal amount, or absence, of a solvent.

In accordance with this invention, a process is provided which comprises producing olefins in the presence of an olefin oligomerization catalyst system and a solvent, wherein said olefin oligomerization catalyst system comprises a chromium source, a pyrrole-containing compound and a metal alkyl, and wherein said solvent is a product of the olefin production process.

In accordance with another embodiment of this invention, a process is provided consisting essentially of producing olefins in the presence of an olefin oligomerization catalyst system and a solvent, wherein said olefin oligomerization catalyst system comprises a chromium source, a pyrrole-containing compound and a metal alkyl, and wherein said solvent is a product of the olefin production process.

DETAILED DESCRIPTION OF THE INVENTION

Catalyst Systems

Catalyst systems useful in accordance with this invention comprise a chromium source, a pyrrole-containing compound and a metal alkyl, all of which have been contacted and/or reacted in the presence of an unsaturated hydrocarbon. Optionally, these catalyst systems can be supported on an inorganic oxide support. These catalyst systems are especially useful for the oligomerization of olefins, such as, for example, ethylene to 1-hexene. As used in this disclosure, the term "oligomerization" broadly encompasses the combination of two olefins (dimerization) to form an olefinic product, three olefins (trimerization) to form an olefinic product and more than three olefins to form an olefinic product, but does not include polymerization of olefins. An oligomer can be defined as a compound, made up of repeating units, whose properties do change with the addition or removal of one or a few repeating units. The properties of a polymer do not change markedly with such a modification.

The chromium source can be one or more organic or inorganic chromium compounds, wherein the chromium oxidation state is from 0 to 6. If the chromium oxidation state is 0, metallic chromium can be the chromium source. Generally, the chromium source can have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

Preferably, the chromium source is a chromium(II)-containing and/or a chromium(III)-containing compound which can yield a catalyst system with improved oligomerization and/or trimerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium(III) 2,2,6,6, -tetramethylheptanedionate [$Cr(TMHD)_3$], chromium(III) 2-ethylhexanoate also called chromium(III) tris(2-ethylhexanoate) [$Cr(EH)_3$], chromium(III) naphthenate [$Cr(Np)_3$], chromium(II) chloride, chromic bromide, chromic fluoride, chromium(III) acetylacetonate, chromium (III) acetate, chromium(III) butyrate, chromium(III) neopentanoate, chromium(III) laurate, chromium(III) stearate, chromium (III) pyrrolides and/or chromium(III) oxalate.

Specific exemplary chromium(II) compounds include, but are not limited to, chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound that will react with the chromium source to form a chromium pyrrolide complex. As used in this disclosure, the term "pyrrole-containing compound" refers to hydrogen pyrrolide, i.e., pyrrole ($C_4H_5N$), derivatives of hydrogen pyrrolide, substituted pyrrolides, as well as metal pyrrolide complexes. A "pyrrolide", as used in this disclosure, is defined as a compound comprising a 5-membered, nitrogen-containing heterocycle, such as for example, pyrrole, derivatives of pyrrole, and mixtures thereof Broadly, the pyrrole-containing compound can be pyrrole and/or any heteroleptic or homoleptic metal complex or salt, containing a pyrrolide radical, or ligand. The pyrrole-containing compound can be either affirmatively added to the olefin production reaction, or generated in-situ.

Generally, the pyrrole-containing compound will have from about 4 to about 20 carbon atoms per molecule. Exemplary pyrrolides include, but are not limited to, and are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, and mixtures thereof. When the pyrrole-containing compound contains chromium, the resultant chromium compound can be called a chromium pyrrolide.

The most preferred pyrrole-containing compounds used in a trimerization catalyst system are selected from the group consisting of hydrogen pyrrolide, i.e., pyrrole ($C_4H_5N$), 2,5-dimethylpyrrole (2,5 DMP) and/or chromium pyrrolides because of enhanced olefin production activity. Optionally, for ease of use, a chromium pyrrolide can provide both the chromium source and the pyrrole-containing compound. As used in this disclosure, when a chromium pyrrolide is used to form a catalyst system, a chromium pyrrolide can be considered to provide both the chromium source and the pyrrole-containing compound. While all pyrrole-containing compounds can produce catalyst systems with high activity and productivity, use of pyrrole and/or 2,5-dimethylpyrrole can produce a catalyst system with enhanced activity and selectivity to a desired product.

The metal alkyl can be any heteroleptic or homoleptic metal alkyl compound. One or more metal alkyls can be used. The alkyl ligand(s) of the metal alkyl can be any aliphatic and/or aromatic radical. Preferably, the alkyl ligand (s) are any saturated or unsaturated aliphatic radical. The metal alkyl can have any number of carbon atoms per molecule. However, due to commercial availability and ease of use, the metal alkyl will usually comprise less than about 70 carbon atoms per metal alkyl molecule and preferably less than about 20 carbon atoms per molecule. Exemplary metal alkyl compounds include, but are not limited to, alkylaluminum compounds, alkylboron compounds, alkylmagnesium compounds, alkylzinc compounds and/or alkyl lithium compounds. Exemplary metal alkyls include, but are not limited to, n-butyl lithium, s-butyllithium, t-butyllithium, diethylmagnesium, diethylzinc, triethylaluminum, trimethylaluminum, triisobutylalumium, and mixtures thereof Preferably, the metal alkyl is selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. The use of hydrolyzed metal alkyls can result is decreased olefin, i.e., liquids, production and increased polymer, i.e., solids, production.

Most preferably, the metal alkyl is a non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaaluminum, tributylaluminum, diethylaluminum chloride, diethylaluminum bromide, diethylaluminum ethoxide, diethylaluminum phenoxide, ethylaluminum dichloride, ethylaluminum sesquichloride, and mixtures thereof for best catalyst system activity and product selectivity. The most preferred alkylaluminum compound is triethylaluminum, for best results in catalyst system activity and product selectivity.

Usually, contacting and/or reacting of the chromium source, pyrrole-containing compound and metal alkyl is done in the presence of an unsaturated hydrocarbon. The unsaturated hydrocarbon can be any aromatic or aliphatic hydrocarbon, in a gas, liquid or solid state. Preferably, to affect thorough contacting of the chromium source, pyrrole-containing compound, and metal alkyl, the unsaturated hydrocarbon will be in a liquid state. The unsaturated hydrocarbon can have any number of carbon atoms per molecule. Usually, the unsaturated hydrocarbon will comprise less than about 70 carbon atoms per molecule, and preferably, less than about 20 carbon atoms per molecule, due to commercial availability and ease of use. Exemplary unsaturated, aliphatic hydrocarbon compounds include, but are not limited to, ethylene, 1-hexene, 1,3-butadiene, and mixtures thereof The most preferred unsaturated aliphatic hydrocarbon compound is 1-hexene, because of elimination of catalyst system preparation steps and 1-hexene can be a reaction product. Exemplary unsaturated aromatic hydrocarbons include, but are not limited to, toluene, benzene, xylene, mesitylene, hexamethylbenzene, and mixtures thereof. Unsaturated, aromatic hydrocarbons are preferred in order to improve catalyst system stability, as well as produce a highly active and selective catalyst system. The most preferred unsaturated aromatic hydrocarbon is toluene.

It should be recognized, however, that the reaction mixture comprising a chromium source, pyrrole-containing compound, metal alkyl and unsaturated hydrocarbon can contain additional components which do not adversely affect and can enhance the resultant catalyst system, such as, for example, halides.

Reactants

Trimerization, as used in this disclosure, is defined as the combination of any two, three, or more olefins, wherein the number of olefin, i.e., carbon-carbon double bonds is reduced by two. Reactants applicable for use in the trimerization process of this invention are olefinic compounds which can a) self-react, i.e., trimerize, to give useful products such as, for example, the self reaction of ethylene can give 1-hexene and the self-reaction of 1,3-butadiene can give 1,5-cyclooctadiene; and/or b) olefinic compounds which can react with other olefinic compounds, i.e., co-trimerize, to give useful products such as, for example, co-trimerization of ethylene plus hexene can give 1-decene and/or 1-tetradecene, co-trimerization of ethylene and 1-butene can give 1-octene, co-trimerization of 1-decene and ethylene can give 1-tetradecene, 1-octadecene and/or 1-docosene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "trimerization" is intended to include dimerization of diolefins, as well as "co-trimerization", both as defined above.

Suitable trimerizable olefin compounds are those compounds having from about 2 to about 30 carbon atoms per molecule and having at least one olefinic double bond. Exemplary mono-1-olefin compounds include, but are not limited to acyclic and cyclic olefins such as, for example, ethylene, propylene, 1-butene, isobutylene, 1-pentene, 4-methyl-1-pentene, 1-hexene, 1-heptene, the four normal octenes, the four normal nonenes, vinylcyclohexane and mixtures of any two or more thereof Exemplary mono-olefins include, but are not limited to, 2-butene, 2-pentene, 2-hexene, 3-hexene, 2-heptene, 3-heptene, cyclohexene and mixtures of two or more thereof. Exemplary diolefin compounds include, but are not limited to, 1,3-butadiene, 1,4- pentadiene, and 1,5-hexadiene. If branched and/or cyclic olefins are used as reactants, while not wishing to be bound by theory, it is believed that steric hindrance could hinder the trimerization process. Therefore, the branched and/or cyclic portion(s) of the olefin preferably should be distant from the carbon-carbon double bond.

Catalyst systems produced in accordance with this invention are particularly suitable for and preferably are employed as trimerization catalyst systems.

Reaction Conditions

The reaction products, i.e., olefin trimers as defined in this specification, can be prepared from the catalyst systems of this invention by solution, slurry, and/or gas phase reaction techniques using conventional equipment and contacting processes. Contacting of the monomer or monomers with a catalyst system can be effected by any manner known in the art. One convenient method is to suspend the catalyst system in an organic medium and to agitate the mixture to maintain the catalyst system in solution throughout the trimerization process. Other known contacting methods can also be employed.

In accordance with another embodiment of this invention, a slurry process can be carried out in a diluent (medium), which is a product of the olefin oligomerization process. Therefor, the choice of reactor diluent, or medium, is based on the selection of the initial olefin reactant. For example, if the oligomerization catalyst is used to trimerize ethylene to 1-hexene, the solvent for the oligomerization reaction would be 1-hexene. If ethylene and hexene were trimerized to produce 1-decene, the oligomerization reaction solvent would be 1-decene. If 1,3-butadiene was trimerized to 1,5-cyclooctadiene, the trimerization reactor solvent would be 1,5-cyclooctadiene.

Optionally, based on economics, a solvent different than one of the oligomerization process products can be used during startup, or initiation, of the oligomerization process. A different inert diluent, such as a paraffin, cycloparaffin, or aromatic hydrocarbon, can be used during the oligomerization process initiation. Exemplary initial reactor diluents include, but are not limited to, isobutane and cyclohexane. Once the reactor has been charged with catalyst, reactant and optional diluent, additional diluent does not need to be and cannot be, added to the reactor. During the course of the oligomerization reaction, the added, inert diluent will become diluted and ultimately removed from the oligomerization process reactor. Reaction temperatures and pressures can be any temperature and pressure which can trimerize the olefin reactants.

Generally, reaction temperatures are within a range of about 0° to about 250° C. Preferably, reaction temperatures within a range of about 60° to about 200° C. and most preferably, within a range of 80° to 150° C. are employed. Too low of a reaction temperature can produce too much undesirable insoluble product, such as, for example, polymer, and too high of a temperature can cause decomposition of the catalyst system and reaction products.

Generally, reaction pressures are within a range of about atmospheric to about 2500 psig. Preferably, reaction pressures within a range of about atmospheric to about 1000 psig and most preferably, within a range of 300 to 700 psig are employed. Too low of a reaction pressure can result in low catalyst system activity.

Optionally, hydrogen can be added to the reactor to accelerate the reaction and/or increase catalyst system activity. If desired, hydrogen also can be added to the reactor to control, i.e. minimize, solids (polymer) production.

Catalyst systems of this invention are particularly suitable for use in trimerization processes.

Products

The olefinic products of this invention have established utility in a wide variety of applications, such as, for example, as monomers for use in the preparation of homopolymers, copolymers, and/or terpolymers.

Further understanding of the present invention and its advantages will be provided by reference to the following examples.

EXAMPLES

Catalyst Preparation

Catalyst system solutions were prepared under an inert atmosphere (nitrogen) at ambient temperatures. Chromium (III) 2-ethylhexanoate ($Cr(EH)_3$) was dissolved in anhydrous toluene (40 mL toluene per 1.0 g of chromium 2-ethylhexanoate) to form a dark green solution; then, 2,5-dimethylpyrrole (2,5-DMP) was added to form a chromium/pyrrole solution. In a separate container, an aluminum alkyl solution was prepared by combining and mixing ethylaluminum dichloride (EADC) and triethylaluminum (TEA). The aluminum alkyl solution then was poured into the chromium/pyrrole solution. The resulting dark yellow-brown solution was stirred for 5 minutes and then the solvent removed invacuo. The remaining oily liquid was diluted with 1-hexene (20 mls 1-hexene per gram $Cr(EH)_3$) and allowed to set overnight. The solution then was filtered to remove a black precipitate; the filtrate, which contained the homogeneous catalyst, was diluted to the desired volume using additional 1-hexene.

Example 1

The catalyst system for each Run was prepared using the component molar ratios given in Table 1. The trimerization reaction conditions and feed rates used for each Run are given in Table 2. Each Run was carried out in a 1-gallon autoclave reactor with an internal cooling coil. The reactor was brought to the desired pressure (see Table 2) with either hexene or cyclohexane prior to the addition of any catalyst system or reactants. As the reaction commenced and continued, if cyclohexane was used, the cyclohexane concentration became negligible due to product formation and withdrawal of reaction product. Ethylene and hydrogen were fed continuously into the reactor through one port and a solution of the catalyst system in 1-hexene was fed through a second port. The product stream was continuously removed through a third port. Catalyst system in the product stream was deactivated by addition of an alcohol. The product stream then was passed through a filter to remove any solid by-products, which generally comprised polymeric products. The composition of the product stream was monitored by GC analysis. The results of each Run are given in Table 3.

TABLE I

Catalyst Components (molar ratios)

|  | Run 101 | Run 102 | Run 103 | Run 104 | Run 105 | Run 106 | Run 107 | Run 108 | Run 109 | Run 110 |
|---|---|---|---|---|---|---|---|---|---|---|
| $Cr(EH)_3$ | 1 | 1 | 1 | 1 | 1 | 1 | 1 | 1 | 1 | 1 |
| 2,5-DMP | 1.8 | 1.8 | 3.0 | 3.0 | 3.0 | 1.8 | 1.8 | 4.0 | 2.9 | 1.8 |
| EADC | 2.5 | 2.5 | 4.0 | 4.0 | 4.0 | 2.5 | 2.5 | 5.0 | 3.8 | 2.5 |
| TEA | 9.0 | 9.0 | 15.0 | 15.0 | 15.0 | 9.0 | 9.0 | 15.0 | 12.0 | 9.0 |

TABLE 2

Run Conditions

|  | Run 101 | Run 102 | Run 103 | Run 104 | Run 105 | Run 106 | Run 107 | Run 108 | Run 109 | Run 110 |
|---|---|---|---|---|---|---|---|---|---|---|
| Temp., °C. | 110 | 115 | 110 | 110 | 125 | 110 | 110 | 110 | 110 | 100 |
| Pressure, psig | 1465 | 1465 | 1200 | 1200 | 1465 | 1465 | 1465 | 1465 | 1465 | 1465 |
| Ethylene feed rate, g/hr | 1022 | 1514 | 2747 | 2004 | 584 | 1022 | 1022 | 1503 | 1277 | 1022 |
| Hydrogen feed rate, liters/hr. | 5.2 | 15.1 | 6.10 | 6.10 | 2.00 | 8.2 | 0.0 | 7.70 | 5.10 | 8.2 |
| Catatyst feed rate, ml/hr | 30 | 24 | 30 | 30 | 30 | 30 | 30 | 30 | 15 | 25 |
| Catalyst residence time, hr. | 1.00 | 0.68 | 0.37 | 0.51 | 0.46 | 1.00 | 1.00 | 0.68 | 0.80 | 1.00 |
| Catatyst concentration, mg Cr/ml | 0.60 | 0.50 | 0.61 | 0.61 | 0.14 | 0.60 | 0.60 | 0.71 | 1.00 | 1.00 |
| ppm Cr in reactor | 17.6 | 8.1 | 6.7 | 9.2 | 7.1 | 17.6 | 17.6 | 14.2 | 12.1 | 24.1 |
| Length of run, hrs | 85.0 | 99.0 | 6.0 | 5.8 | 6.0 | 7.5 | 7.5 | 6.0 | 7.1 | 7.3 |

TABLE 3

Product Data

|  | Run 101 | Run 102 | Run 103 | Run 104 | Run 105 | Run 106 | Run 107 | Run 108 | Run 109 | Run 110 |
|---|---|---|---|---|---|---|---|---|---|---|
| Ethylene conversion, % | 85.5 | 80.2 | 64.2 | 72.3 | 69.3 | 83.4 | 87.5 | 77.9 | 82.0 | 92.2 |
| Olefin distribution, wt % |  |  |  |  |  |  |  |  |  |  |
| butenes | 0.2 | 0.4 | 0.1 | 0.2 | 0.2 | 0.4 | 0.1 | 0.2 | 0.3 | 0.4 |
| 1-hexene | 85.0 | 84.6 | 88.6 | 83.5 | 88.4 | 84.6 | 80.3 | 86.9 | 85.8 | 67.8 |
| intetnal hexenes | 0.5 | 0.8 | 0.7 | 0.7 | 0.7 | 0.8 | 0.5 | 0.7 | 0.6 |  |
| octenes | 0.5 | 0.6 | 0.5 | 0.1 | 0.6 | 0.3 | 0.2 | 0.4 | 0.4 | 0.6 |
| decenes | 12.8 | 12.4 | 9.4 | 14.5 | 9.7 | 12.6 | 16.8 | 10.8 | 11.6 | 24.6 |
| tetradecenes | 1.0 | 1.2 | 0.9 | 1.0 | 0.5 | 1.3 | 2.2 | 0.9 | 1.3 | 5.6 |
| Purity of hexene fraction,(a) % | 99.4 | 99.0 | 99.2 | 99.2 | 99.3 | 99.0 | 99.4 | 99.2 | 99.3 | 98.5 |
| Productivity, g $C_6^=$/gCr-hr | 48400 | 101000 | 85100 | 65700 | 86700 | 40000 | 39800 | 47600 | 58300 | 25900 |
| Total polymer, g | 15.3 | 61.4 | 3.5 | 3.9 | 0.6 | 1.2 | 0.9 | 4.2 | 0.4 | 0.7 |

(a)Percentage of hexenes that are 1-hexene.

For comparative purposes, note that the molar ratios of the catalyst components, as shown in Table 1, in Runs 101, 102, 106, 107 and 110 were identical and that the molar ratios of the catalyst components in Runs 103, 104 and 105 also were identical. Table 2 shows that Runs 103 and 104 were at a lower pressure; Runs 102, 103, 104 and 105 had a lower chromium concentration in the reactor; Runs 102 and 105 were at higher temperatures; Run 110 was at a lower temperature; and that Run 107 had no hydrogen added to the reactor.

The data in Table 3 teaches, as demonstrated in Runs 101, 102, 106, 107 and 1 10, that excess chromium can lower 1-hexene production and, therefore, result in a lower purity of the hexene fraction. However, excess chromium, as in Runs 101, 102, 106, 107 and 110, also can increase reactant conversion and produce more decenes in the liquid product. Increasing hydrogen mole fraction in the reactor feed can decrease the percent purity of 1-hexene in the product stream, as shown by Runs 101, 106 and 107.

Example 2

Designed Experiment

A five factor, three level, central composite design with four center point replicates was used (30 runs total). The data was computer fit using the Strategy program, by David Doehlert, available from Experiment Strategies Foundation, P.O. Box 27254, Seattle, Wash. The results of the designed experiment are given, below, in Table 4. The factors and ranges used in the designed experiment, as indicated in the second through sixth columns in Table 4, were:

| Factor | Range |
| --- | --- |
| Catalyst molar ratios of components | Cr:2,5-DMP:EADC:TEA |
| Hydrogen concentration in reactor | 0 to 0.01 moles $H_2$/liter |
| Chromium concentration in reactor | 6.5 to 13 $\mu$moles Cr/liter |
| Space (residence) time in reactor | 0.6 to 1 hour |
| Reactor temperature | 100 to 120° C. |

TABLE 4

| Run | Cat | $H_2$ | Cr | R Time | Temp | $C_6$ | R Vol | Conv | Prod | T Prod | Lbs Cr | T Poly | R Poly | F Poly |
| --- | --- | --- | --- | --- | --- | --- | --- | --- | --- | --- | --- | --- | --- | --- |
| 201 | 1 | 0 | 13 | 0.6 | 120 | 81.43 | 4765 | 85.89 | 28970 | 2545 | 3452 | 2.12 | 0.39 | 1.73 |
| 202 | -1 | 0.01 | 13 | 0.6 | 120 | 78.43 | 4969 | 85.5 | 27775 | 3984 | 3600 | 0.85 | 0.04 | 0.81 |
| 203 | 1 | 0.01 | 6.5 | 1 | 100 | 80.85 | 8464 | 81.17 | 54362 | 4775 | 1840 | 0.79 | 0.04 | 0.75 |
| 204 | 0 | 0.005 | 9.75 | 0.8 | 110 | 65.71 | 7473 | 90.48 | 32836 | 3578 | 3045 | 1.8 | 0.01 | 1.79 |
| 205 | 1 | 0.01 | 6.5 | 0.6 | 120 | 79.74 | 51.96 | 80.43 | 53130 | 4667 | 1882 | 2.38 | 0.02 | 2.36 |
| 206 | -1 | 0 | 6.5 | 0.6 | 120 | 80.43 | 4854 | 85.36 | 56877 | 8159 | 1758 | 2.37 | 1.53 | 0.84 |
| 207 | 0 | 0.005 | 9.75 | 1 | 110 | 66.21 | 9225 | 90.94 | 33251 | 3623 | 3007 | 0.07 | 0.07 | 0 |
| 208 | 1 | 0 | 6.5 | 1 | 120 | 76.62 | 8527 | 85.01 | 53956 | 4739 | 1853 | 1.26 | 1.08 | 0.18 |
| 209 | -1 | 0 | 13 | 0.6 | 100 | 82.8 | 4747 | 84.79 | 29077 | 4171 | 3439 | 1.38 | 0.61 | 0.77 |
| 210 | 1 | 0 | 6.5 | 0.6 | 100 | 83.77 | 4609 | 86.32 | 59899 | 5261 | 1669 | 1.05 | 1.05 | 0 |
| 211 | -1 | 0.01 | 6.5 | 0.6 | 100 | 89.06 | 4860 | 86.39 | 56801 | 8148 | 1761 | 0.6 | 0.6 | 0 |
| 212 | -1 | 0 | 6.5 | 1 | 100 | 78.2 | 7982 | 76.99 | 57640 | 8268 | 1735 | 3.39 | 1.75 | 1.63 |
| 213 | 0 | 0.01 | 9.75 | 0.8 | 110 | 76.16 | 6547 | 88.97 | 37483 | 4084 | 2668 | 0.47 | 0.37 | 0.1 |
| 214 | 0 | 0.005 | 9.75 | 0.8 | 110 | 80.09 | 6284 | 89.12 | 39047 | 4254 | 2561 | 0.04 | 0.04 | 0 |
| 215 | 1 | 0 | 13 | 1 | 100 | 72.9 | 8285 | 88.28 | 27766 | 2439 | 3602 | 1.02 | 0.37 | 0.64 |
| 216 | -1 | 0.01 | 6.5 | 1 | 120 | 87.89 | 8826 | 91.95 | 52128 | 7478 | 1918 | 0.47 | 0.26 | 0.21 |
| 217 | -1 | 0 | 13 | 1 | 120 | 78.1 | 8066 | 71.6 | 28520 | 4091 | 3506 | 2.45 | 1.32 | 1.13 |
| 218 | 0 | 0 | 9.75 | 0.8 | 110 | 76.06 | 6836 | 88.16 | 35897 | 3911 | 2786 | 1.62 | 1.21 | 0.41 |
| 219 | 0 | 0.005 | 9.75 | 0.8 | 100 | 83.81 | 6365 | 85.46 | 38550 | 4200 | 2594 | 1.74 | 1.16 | 0.58 |
| 220 | -1 | 0.005 | 9.75 | 0.8 | 110 | 80.02 | 6019 | 83.29 | 40765 | 5848 | 2453 | 0.3 | 0.05 | 0.25 |
| 221 | 0 | 0.005 | 9.75 | 0.6 | 110 | 82.64 | 4746 | 92.24 | 38778 | 4225 | 2579 | 0.3 | 0.3 | 0 |
| 222 | 0 | 0.005 | 13 | 0.08 | 110 | 79.24 | 6458 | 84.97 | 28496 | 3105 | 3509 | 3.14 | 0.08 | 3.06 |
| 223 | 0 | 0.005 | 6.5 | 0.8 | 110 | 85.79 | 6316 | 86.83 | 58275 | 6350 | 1716 | 0.8 | 0.37 | 0.43 |
| 224 | 1 | 0.005 | 9.75 | 0.8 | 110 | 80.27 | 6441 | 82 | 38096 | 3346 | 2625 | 4.03 | 0.19 | 3.85 |
| 225 | -1 | 0.01 | 13 | 1 | 100 | 67.79 | 8885 | 85.94 | 25890 | 3714 | 3862 | 1.86 | 0.81 | 1.05 |
| 226 | 1 | 0.01 | 13 | 1 | 120 | 65.8 | 9402 | 92.21 | 24468 | 2149 | 4087 | 3.34 | 0.03 | 3.31 |
| 227 | 0 | 0.005 | 9.75 | 0.8 | 120 | 71.27 | 7029 | 89.77 | 34912 | 3804 | 2864 | 1.93 | 0.03 | 1.9 |
| 228 | 1 | 0.01 | 13 | 0.6 | 100 | 78.5 | 4826 | 88.7 | 28600 | 2512 | 3497 | 0.94 | 0.54 | 0.4 |
| 229 | 0 | 0.005 | 9.75 | 0.8 | 110 | 69.38 | 7130 | 87.96 | 34415 | 3750 | 2906 | 1.68 | 0 | 1.68 |
| 230 | -1 | 0.005 | 9.75 | 0.8 | 110 | 76.38 | 66.81 | 89.81 | 36728 | 5269 | 2723 | 0.03 | 0.03 | 0 |

"Cat" is molar ratio of catalyst components (Cr:2,5-DMP:EADC:TEA) formulation;
-1 is 1:1:1.8:2.5:9
0 is 1:2.9:3.8:12
1 is 1:4:5:15
"H2" is hydrogen mole fraction in all feed streams to reactor, moles $H_2$.
"Cr" is chromium mole fraction in all feed streams to reactor, x $10^{-6}$ moles Cr.
"RTime" is space (residence) time in reactor of reactants, hours.
"Temp" is reactor temperature, °C.
"C6" is selectivity in product stream to 1-hexene, weight percent.
"Vol" is reactor volume for a 100 million pounds 1-hexene per year, gallons.
"Conv" is percent of ethylene converted to any product, including hexene, weight percent.
"Prod" is productivity and is the amount of 1-hexene produced relative to grams of chromium in the catalyst, grams 1-hexene/grams Cr.
"TProd" is productivity of all metals in the reactor, grams hexene/grams metals.
"LbsCr" is minimum amount of chromium needed per year for a 100 million pound 1-hexene plant, pounds.
"TPoly" is total polymer produced per hour period for a 100 million pound per year 1-hexene plant, grams/hour; note that RPoly plus FPoly equal TPoly.
"RPoly" is total polymer produced in the reactor per hour period for a 100 million pound per year 1-hexene plant, grams/hour.
"FPoly" is polymer filtered out of product stream (an assumption was made that all solids in the product stream were polymer) hour period for a 100 million pound per year 1-hexene plant, grams/hour.

The results of the designed experiment support the data found in the previous examples. In general, minimizing chromium concentration will minimize the chromium waste, maximum selectivity can be obtained by minimizing chromium concentration and minimizing the space (residence) time, and minimum polymer production can be achieved by increasing hydrogen concentration and medium to high chromium concentration. As used herein, references to "concentration" are in terms of concentration in the reactor vessel. The optimum operating parameters, to minimize waste and polymer production, with acceptable activity and selectivity, based on the designed experiment, are as follows:

Chromium concentration: 6.5 to $8 \times 10^{-6}$ mole fraction

Hydrogen concentration: 0.005 to 0.013 mole fraction

Space time: up to 0.07 hours

Temperature: about 115° F. (about 46° C.)

Catalyst composition (approximate mole ratios):

Cr=1:2,5-DPM=1.8:EADC=2.5:TEA=9

Cr is chromium; 2,5-DMP is 2,5-dimethylpyrrole; EADC is ethylaluminum dichloride; TEA is triethyl aluminum.

While this invention has been described in detail for the purpose of illustration, it is not to be construed as limited thereby but is intended to cover all changes and modifications within the spirit and scope thereof.

That which is claimed is:

1. A process to oligomerize olefins under effective olefin oligomerization conditions in the presence of a homogeneous olefin oligomerization catalyst system comprising contacting said catalyst system with an olefin in a solvent; wherein said catalyst system comprises
    a) a chromium source selected from the group consisting of chromium metal and a chromium salt having the formula $CrX_n$, wherein X can be the same or different and is an organic or inorganic radical and n is an integer from 1 to 6;
    b) a pyrrole-containing compound; and
    c) an alkyl compound; and
    wherein said solvent consists essentially of a product of said olefin oligomerization process.

2. A process according to claim 1 wherein said oligomerization process is a trimerization process.

3. A process according to claim 1 wherein said chromium source is selected from the group consisting of chromium (II)-containing compounds, chromium(III)-containing compounds, and mixtures thereof.

4. A process according to claim 3 wherein said chromium source is a chromium(III)-containing compound selected from the group consisting of chromium carboxylates, chromium naphthanates, chromium halides, chromium pyrrolides, chromium dionates and mixtures of two or more thereof.

5. A process according to claim 4 wherein said chromium sources selected from the group consisting of chromium(III) 2,2,6,6-tetramethylheptanedionate [Cr(TMHD)$_3$], chromium(III) 2-ethylhexanoate Cr(EH)3 or chromium(III) tris(2-ethylhexanoate), [chromium(III) naphthanate [Cr(Np)3)$_3$], chromnium(III) chloride, chromic bromide, chromic fluoride, chromium (III) acetylacetonate, chromium(III) acetate, chromium(III) butyrate, chromium(III) neopentanoate, chromium(III) laurate, chromium(III) stearate, chromium(III) pyrrolides, chromium(III) oxalate, and mixtures of two or more thereof.

6. A process according to claim 1 wherein said alkyl compound is a non-hydrolyzed metal alkyl and is selected from the group consisting of alkyl aluminum compounds, alkyl boron compounds, alkyl magnesium compounds, alkyl zinc compounds, alkyl lithium compounds, and mixture of two or more thereof.

7. A process according to claim 6 wherein said non-hydrolyzed metal alkyl is an alkylaluminum compound.

8. A process according to claim 7 wherein said alkyl aluminum compound is triethylaluminum.

9. A process according to claim 1 wherein said pyrrole-containing compound is selected from the group consisting of pyrrole, derivatives of pyrrole, alkali metal pyrrolides, salts of alkali metal pyrrolides, and mixtures thereof.

10. A process according to claim 9 wherein said pyrrole-containing compound is selected from the group consisting of hydrogen pyrrolide, 2,5-dimethylpyrrole, and mixtures thereof.

11. A process according to claim 1 wherein said catalyst system further comprises a halide source.

12. A process according to claim 1 wherein said olefin has from about 2 to about 30 carbon atoms per molecule.

13. A process according to claim 12 wherein said olefin is ethylene.

14. A process according to claim 1 wherein said solvent is an olefin having from about 2 to about 30 carbon atoms per molecule.

15. A process according to claim 14 wherein said solvent is 1-hexene.

16. A process to oligomerize olefins under effective olefin oligomerization conditions in the presence of a homogeneous olefin oligomerization catalyst system consisting essentially of contacting said catalyst system with an olefin in a solvent; wherein said catalyst system comprises a chromium source selected from the group consisting of chromium metal and a chromium salt having the formula $CrX_n$, wherein X can be the same or different and is an organic or inorganic radical and n is an integer from 1 to 6, a pyrrole-containing compound that will react with the chromium source to form a chromium-pyrrolide complex and an alkyl compound; and
    wherein said solvent consists essentially of a product of said olefin oligomerization process.

* * * * *